(12) United States Patent
Wright

(10) Patent No.: US 8,071,283 B2
(45) Date of Patent: Dec. 6, 2011

(54) METHODS AND APPARATUS FOR SCREENING FOR CHROMOSOMAL ABNORMALITIES

(75) Inventor: David Edmund Wright, Ivybridge (GB)

(73) Assignee: University of Plymouth, Plymouth, Devon (GB)

( * ) Notice: Subject to any disclaimer, the term of this patent is extended or adjusted under 35 U.S.C. 154(b) by 0 days.

(21) Appl. No.: 12/986,534

(22) Filed: Jan. 7, 2011

(65) Prior Publication Data

US 2011/0246077 A1 Oct. 6, 2011

Related U.S. Application Data

(63) Continuation of application No. 10/565,686, filed as application No. PCT/GB2004/003013 on Jul. 12, 2004, now abandoned.

(30) Foreign Application Priority Data

Jul. 25, 2003 (GB) ................................ 0317476.0

(51) Int. Cl.
*C12Q 1/00* (2006.01)
*G01N 33/76* (2006.01)
*G01N 33/50* (2006.01)

(52) U.S. Cl. ...................... 435/4; 436/811; 436/814
(58) Field of Classification Search .................. 422/64; 435/4; 436/65, 63, 174, 906, 510
See application file for complete search history.

(56) References Cited

U.S. PATENT DOCUMENTS 5,906,944 A 5/1999 Davies

FOREIGN PATENT DOCUMENTS

| EP | 0800085 A2 | 10/1997 |
|---|---|---|
| WO | 9956132 A1 | 11/1999 |

OTHER PUBLICATIONS

Benattar et al., "Efficiency of Ultrasound and Biochemical Markers for Down's Syndrome Risk Screening. A Prospective Study," Fetal Diagnosis and Therapy, 14:112-117, 1999.
International Search Report and Written Opinion for International Patent Application No. PCT/GB20041003013, mailed from the International Searching Authority on Nov. 8, 2005, 10 pgs.
EPO Communication for EP Application No. 04743354.5 mailed Dec. 12, 2010 regarding observations by a third party concerning the patentability of the invention, 4 pgs.
Wright et al., "Cross-trimester repeated measures testing for Down's syndrome screening: an assessment," Health Technology Assessment, vol. 14, No. 33, 92 pgs., Jul. 2010.

*Primary Examiner* — Christine T Mui
(74) *Attorney, Agent, or Firm* — K&L Gates LLP

(57) ABSTRACT

This invention generally relates to methods, apparatus, and computer program code for antenatal screening for chromosomal abnormalities, in particular Down's Syndrome. A method of determining a likelihood of a fetus carried by a pregnant mother having a chromosomal abnormality, a first biological, parameter being suitable for screening said fetus for said chromosomal abnormality, the method comprising: receiving first data from a first stage of pregnancy of said mother, said first data comprising data representing a first value of said first biological parameter; receiving second data from a second, later stage of said pregnancy, said second data comprising data representing a second value of said first biological parameter; and determining likelihood data from said first and second data, said likelihood data representing the likelihood of said fetus having a chromosomal abnormality.

21 Claims, 7 Drawing Sheets

METHODS AND APPARATUS FOR SCREENING FOR CHROMOSOMAL ABNORMALITIES

REFERENCE TO RELATED APPLICATIONS

This application is a continuation of U.S. patent application Ser. No. 10/565,686, filed Jan. 24, 2006, which is a national phase application of International Patent Application No. PCT/GB2004/003013, filed Jul. 12, 2004, which claims priority to and the benefit of Great Britain Patent Application No. 0317476.0, filed Jul. 25, 2003, the entire disclosures of each of which are incorporated by reference herein.

This invention generally relates to methods, apparatus, and computer program code for antenatal screening for chromosomal abnormalities, in particular Down's Syndrome.

A recent large-scale study by Wald et al. commissioned by the UK National Health Service Health Technology Assessment Program aimed to identify the most effective, safe and cost-effective method of antenatal screening for Down's Syndrome using nuchal translucency (NT), maternal serum and urine markers in the first and second trimesters of pregnancy, and maternal age in various combinations (Wald N J, Rodeck C, Hackshaw A K, Walters J, Chitty L, Mackinson A M, "First and second trimester antenatal screening for Down's syndrome: the results of the Serum, Urine and Ultrasound Screening Study (SURRUS)", *Health Technology Assessments* 2003:7(11); http://www.hta.nhsweb.nhs.uk; see also Wald N J, Watt H C, Hackshaw A K, "Integrated screening for Down's syndrome based on tests performed during the first and second trimesters", N Engl J Med 1999:341:461-7).

The study concluded that an integrated test using measurements of four biochemical markers all at 14-20 weeks gestation with the ultrasound marker NT and a fifth biochemical marker measured at 10 completed weeks provided the most effective and safe method of screening (see, for example, the executive summary of Wald et at at page (iv)). Patent protection for the technique was sought (WO99/56132; U.S. Pat. No. 6,573,103).

A number of tests for antenatal screening for Down's Syndrome are known. The so-called combined test is a first trimester test based upon combining nuchal translucency measurement with free β-human chorionic gonadotrophin (β-hCG), pregnancy-associated plasma protein A (PAPP-A) and maternal age. The quadruple test is a second trimester test based on measurement of AFP (α-fetoprotein), unconjugated oestriol ($uE_3$), free β-hCG (or total hCG), and inhibin-A together with maternal age. The integrated test integrates measurements performed during the first and second trimester of pregnancy into a single test result and performs better than either than the combined or quadruple test alone. Generally "integrated test" refers to the integration of nuchal translucency and PAPP-A measurements in the first trimester with the quadruple test markers in the second. The nuchal translucency (NT) measurement is a measurement of the width of an area of translucency at the back of the foetal neck, usually measured at about 10-13 weeks of pregnancy using ultrasound. Various other forms of tests are also known such as the so-called triple test, the double test, and the serum integrated test (a variant of the integrated test using serum markers only—PAPP-A in the first trimester and the quadruple test markers in the second trimester).

A good antenatal screening test has a good true-positive rate (a true-positive is an affected pregnancy with a positive test result) and a low-false positive rate (a false-positive is an unaffected pregnancy with a positive test result). A cut-off level is chosen to define a positive result and distinguish it from a negative result. With a single marker this comprises a specified level of the marker; with tests based on a combination of markers this generally comprises a form of risk estimate. An affected pregnancy in this context is a pregnancy with a fetus with a chromosomal abnormality and the techniques described herein are particularly applicable to Down's Syndrome, that is trisomy of chromosome 21.

A detection rate, that is a rate of detection of affected pregnancies, may also be defined so that, for example, a detection rate of 85 percent implies that fifteen percent of affected pregnancies will not be detected by a test. There is a relationship between detection rate and false-positive rate which is given by a so-called ROC (Receiver Operating Characteristic) curve for the test. There is a human and financial cost associated with both false-positive and missed detections. The human cost of a missed detection rate of, say, fifteen percent is easy to appreciate. The financial cost of a false-positive relates to follow-up procedures since a positive test result is generally further investigated by amniocentesis or CVS (Choronic Villus Sampling), which have a financial cost and also an associated risk of miscarriage (approximately one percent).

The present inventor has re-analysed the data from the Wald study and has identified a new approach to the determination of chromosomal abnormalities which can provide significantly better results than the procedures of Wald, based upon a counter-intuitive recognition of the way in which the data can be utilised.

As mentioned above there are a number of more or less standard biochemical and ultrasound markers for Down's Syndrome. Generally these markers are effective as markers at only one stage or trimester of pregnancy although one, free β-hCG is effective in both the first and second trimesters.

Broadly speaking the approach of Wald et al is to pick the best individual markers at each stage of pregnancy and to combine these into a single, integrated screening test. Wald does not use markers which are ineffective at any particular stage and furthermore teaches against the use of highly correlated markers (see, for example, WO' 132 at page 8 lines 20-23), broadly because one would expect markers which are correlated with one another to provide little new information.

The present inventor has recognised, however, that this approach conceals two statistical fallacies and that using data relating to a level of a marker (perhaps here better termed a feature) from a stage of pregnancy at which the marker is substantially ineffective can lead significant benefits in screening performance. It has further been recognised that it is helpful if parameters ("markers" or "features") measured at two different gestational ages are highly correlated with one another because (as will be explained further below) this enables some degree of compensation for natural variations in a parameter between subjects.

Thus we will describe methods (and computer programmes and corresponding apparatus) in which repeated measurements of one or more biological parameters of a fetus are made at different stages of a pregnancy, in one of the stages the parameter or parameters acting as a marker for a chromosomal abnormality, in particular Downs Syndrome, in the other of the stages the parameter not having any significant value as such as a marker. The parameters are preferably levels of biological chemicals associated with pregnancy. Preferably these are highly correlated since, broadly speaking, the stronger the correlation the more discrimatory power. The parameters are preferably normalised for gestational age of the fetus and, optionally, for other factors such as maternal weight and smoking status.

To aid understanding of embodiments of the invention described later it is helpful to explain the origin of the two above mentioned statistical fallacies.

The fallacy of high correlations is that "a second marker adds little to the first if the correlation between the markers in Down's syndrome and unaffected pregnancies is high". 'If two variables are perfectly correlated one adds nothing to the other in determining risk . . . '—Wald et al. (1988)).

The statement of Wald et al. (1988) is correct—it is the case that if there is a perfect relationship between two features then knowledge of one determines the other so one of the features is redundant. Similarly, if there is a near perfect relationship, one feature adds very little to the other. However, in screening the strength of association is usually measured in terms of separate correlations for Down syndrome outcomes and unaffected outcomes. In cases where these correlations are high and the underlying relationships are different in Down's syndrome and unaffected pregnancies, the joint values are generally highly discriminatory. This is illustrated for the case of first and second trimester PAPP-A measurements in FIG. 1.

Levels of biological markers are generally given as a logarithm (base 10 or natural) of an MoM (Multiple of Median) value. FIG. 1a shows samples of log(MoM PAPP-A) in the first (horizontal axis) and the second (vertical axis) trimesters for 1000 Down's syndrome pregnancies 10 and 1000 unaffected pregnancies 20. These samples were drawn from bivariate Gaussian distributions using parameter estimates taken from Wald et al. (2003). The ellipse represents the 90% contour containing 90% of the distribution of values. FIG. 1b demonstrates what happens when the correlations in Down's syndrome and unaffected pregnancies are increased to 0.95. If this were the case discrimination would be almost perfect. FIG. 1c illustrates what happens when the correlations in Down's syndrome and unaffected pregnancies are zero. In this case the discriminatory power is worse than in FIG. 1a.

The second fallacy is that "if a feature has no discriminatory power when viewed in alone, it has no discriminatory power when used jointly with other features"; this is addressed using the same example of PAPP-A. In the second trimester PAPP-A has little or no discriminatory power but when used in conjunction with the first trimester PAPP-A values it greatly enhances discriminatory power. In fact for an 85% detection rate the FPR for PAPP-A in the first trimester, using the parameters of Wald et al (2003), when applied to the maternal age distribution of England and Wales (1996 to 1998) is 17%. Using PAPP-A in the first and second trimester reduces the false positive rate for an 85% detection rate to 1.9%. The way the second trimester measure increases discrimination is illustrated in FIG. 2. FIG. 2a shows samples of log(MoM PAPP-A) in first (horizontal axis) and second trimester (vertical axis) for 1000 Down's syndrome pregnancies 10 and 1000 unaffected pregnancies 20. These values were drawn from the distributions fitted by Wald et al. (2003). Projecting the points onto the horizontal axis there is clearly a good discrimination PAPP-A in the first trimester. Projecting points onto the vertical axis there is very little discriminatory power with second trimester PAPP-A. However, the joint distribution separates Down's from unaffected pregnancies much more effectively than PAPP-A in trimester 1. FIG. 2b shows a hypothetical situation in which PAPP-A is assumed to have the same median MoM in the second trimester as it does in the first. In this case there is more overlap in the joint distribution than there is in FIG. 2a. FIG. 2c shows a hypothetical situation in which the median MoM for PAPP-A in the second trimester is in the opposite direction to that in the first. This situation would give near perfect discrimination.

Broadly speaking referring to the above scattergraphs although two distributions may overlap when projected on to one or other axis the points representing unaffected and affected pregnancies may nonetheless lie on separable lines and the higher the correlation coefficient the better the lines can be separated. The value of measuring the level of a biological parameter ("marker" or "feature") at a stage of pregnancy where the parameter is ineffective as a marker can be understood by considering a (much simplified) example. Consider a syndrome which has the effect of making a child unnaturally shorter at the age of five, but which has no effect on a child of age ten. The height of a child is a feature that varies considerably between children but and it is difficult on the basis of a short height at 5 years to distinguish between those children that are naturally short and those that have the syndrome. However by making measurements on the same child at age five and at age ten the age ten height can effectively be used as a yardstick to normalise the height measurement at age five and hence better determine whether or not the child at age five is abnormally small.

A number of features have similar characteristics to PAPP-A in that (a) first and second trimester log (MoM) values are highly correlated in both Down's syndrome and unaffected pregnancies and (b) they discriminate in one trimester but not the other.

According to a first aspect of the present invention there is therefore provided a method of determining a likelihood of a fetus carried by a pregnant mother having a chromosomal abnormality, a first biological, parameter being suitable for screening said fetus for said chromosomal abnormality, the method comprising: receiving first data from a first stage of pregnancy of said mother, said first data comprising data representing a first value of said first biological parameter; receiving second data from a second, later stage of said pregnancy, said second data comprising data representing a second value of said first biological parameter; and determining likelihood data from said first and second data, said likelihood data representing the likelihood of said fetus having a chromosomal abnormality.

In embodiments of the method by making repeated measurements of the same biological parameter at different stages, enhance discriminatory power is achieved and for a given detection rate the false positive rate may be reduced as compared with the above mentioned integrated test. The biological parameter is preferably a marker for the chromosomal abnormality at one of the first and second stages of pregnancy but preferably has substantially no value as a marker at a time during the other of the first and second stages of pregnancy. The first and second stages of pregnancy preferably comprise first and second trimesters of the pregnancy, generally taken for a human being as being from 8-13 weeks and from 14 to 22 weeks of the pregnancy respectively. Whether or not the biological parameter has a value as a marker may be judged at a reference point during one or both of the stages of pregnancy, for example at the ten week point during the first trimester and, for example, at the 14, 18 or 22 week point during the second trimester (or an average of the value of the parameter as a marker during a stage of pregnancy may be employed).

The value of a biological parameter as a marker is generally expressed as a logarithm of a multiple of median value, that is a median value for the biological parameter is determined adjusted for gestational age of the fetus and, optionally, for maternal-related factors such as weight, smoking status and the like. A measured value of the parameter may then be expressed as a multiple of the expected median (or other average) value (MoM) so that if the measured value is equal to the expected value the MoM value is equal to 1.0 and the log MoM value is equal to zero. Thus a smaller than expected measured value results in a negative log MoM median marker level and a greater than expected value a positive log MoM median marker level.

Whether a parameter measured at a particular stage of pregnancy has substantial value as a marker when used individually is determined largely from the mean log MoM in affected pregnancies. If this is small in absolute magnitude relative to the standard deviation of the log MoM values, then the parameter will individually have little value. Preferred embodiments of the method described here rely on the use of repeated measures that have mean log MoM values at one stage of pregnancy that differ from zero by less than, in order of increasing preference, 100%, 90%, 50%, and 25% of a standard deviation. For example, a parameter may be considered a useful marker for Down's syndrome pregnancies if during a stage of pregnancy it differs from zero by more than 90% of the standard deviation in Down's syndrome pregnancies. Thus a marker may be considered as having substantially no value if at a point during a stage of pregnancy the logarithm MoM value is not substantially different from zero, that is if the logarithm MoM value is less than one standard deviation, preferably 0.9 standard deviation, more preferably 0.5 standard deviation, still more preferably 0.25 of a standard deviation (SD) from zero in affected pregnancies.

Median marker level data and standard deviation data for a range of biochemical markers may be found in Wald et al (HTA 2003, 7(11), ibid) tables 33 and 34 specifically hereby incorporated by reference. Gestational age may be based upon either the first day of the last menstrual period (LMP) or on an ultrasound scan measure of the fetus, generally a BPD (biparietal diameter) or a CRL (crown-rump length) measurement.

In other less preferred implementations of the method where the biological parameter or parameters comprise one or more of $uE_3$, total hCG, free $\beta$-hCG, inhibin A and PAPP-A the biological parameter may be chosen such that its log base ten multiple of median value when determined using a model according to any one of the relevant equations given later (based upon gestational age (in days) determined by either LMP or an ultrasound measure of the fetus) has an absolute value of less than 0.1 during one of the stages of pregnancy and an absolute value of greater than 0.1 during the other of the said stages of pregnancy. However more generally it is preferred that the difference from zero is measured in SD units as if a marker has very little variation then a log MoM value of 0.1 may be highly discriminatory.

Whether the parameter has substantially no value as a marker may be further alternatively determined by comparison with the value of the parameter as a marker in another stage of pregnancy so that, for example, the parameter may be considered as having substantially no value as a marker if the $\log_{10}$ MoM value is a factor of two, or preferably five less at one stage of pregnancy than another.

Preferably the biological parameter is selected such that a correlation coefficient of the first and second values of the parameter (either in a cohort of pregnancies having the abnormality or in a cohort without the abnormality) is greater than, in order of increasing preference, 0.3, 0.5, 0.6, 0.8.

The method may employ any of the conventional markers mentioned above including (but not limited to) total hCG, PAPP-A, Inhibin-A, AFP, and $uE_3$. Preferably free $\beta$-hCG is not used as this has value as a marker at both the first and second stages of pregnancy.

In a preferred embodiment of the method first and second values of a second biological parameter (different to the first parameter) are measured and used to determine the likelihood data. This likelihood data preferably represents a likelihood ratio that can be combined with a maternal age specific risk to produce a posterior risk of the fetus having a chromosomal abnormality. Like the first parameter the second parameter preferably has value as a marker for the chromosomal abnormality at one stage of the pregnancy but not at another. In this way the number of false positives can be further reduced. Optionally parameter data from an ultrasound measurement such as nuchal transparency (NT) may also be included.

Based upon a re-analysis of the results of Wald et al (ibid) some particularly preferred combinations of parameters are: PAPP-A$^2$+uE3$^2$; PAPP-A$^2$+Inhibin$^2$+uE3$^2$; Total hCG$^2$+PAPP-A$^2$, preferably+uE3$^2$; and PAPP-A$^2$+uE3$^2$+NT (where "$^2$" indicates a repeated measure, one at each of the first and second trimesters and "+" indicates a combination of two or more parameters).

The second biological parameter is preferably selected in a corresponding manner to the first biological parameter. To improve the screening performance further an ultrasound measurement such as NT may also be incorporated into the combination.

The likelihood (ratio) data may be determined according to a range of techniques. In a preferred technique the parameter value data is adjusted for gestational age of the fetus and optional maternal covariates (i.e. to form multiple of median data) and then a probability of the measured (adjusted) parameter values for unaffected and affected pregnancies is determined and the ratio of these two probabilities used to calculate a likelihood ratio, for example that the pregnancy is either unaffected or affected. Preferably this likelihood ratio is then combined with (adjusted by) a prior probability dependent upon maternal age to provide a posterior likelihood or risk that the pregnancy is affected (or unaffected), which may then be provided either to a clinician or to a parent in a variety of different forms.

In another aspect the invention provides a method of determining whether a pregnant woman is at an increased risk of having a fetus with Down's Syndrome, the method comprising the steps of measuring at least one screening marker level from one of a first and second stage of pregnancy by assaying a sample obtained from the pregnant woman at said first or second stage of pregnancy for at least one biochemical screening marker; measuring a level of the same said at least one screening marker at the other of said first and second stage of pregnancy by assaying a sample obtained from the pregnant woman at said other stage of pregnancy for said at least one biochemical screening marker; and determining a quantitative estimate of the risk of Down's Syndrome using the measured screening marker levels from both the first and second stages of pregnancy.

The invention further provides a method of determining whether a pregnant woman is at an increased risk of having a fetus with Down's Syndrome, the method comprising the steps of: measuring at least one screening marker level from one of a first and second stage of pregnancy by assaying a sample obtained from the pregnant woman at said first or second stage of pregnancy for at least one biochemical screening marker; determining a first quantitative estimate of the risk of Down's syndrome using said measured screening marker level from the first stage of pregnancy; measuring a level of the same said at least one screening marker at a second stage of pregnancy by assaying a sample obtained from the pregnant woman at said second stage of pregnancy for said at least one biochemical screening marker; and determining a quantitative estimate of the risk of Down's Syndrome using the measured screening marker levels from both the first and second stages of pregnancy.

The above described methods may be implemented on a general purpose computer system using processor control code which may be provided on a data carrier such as a disk, CD- or DVD-ROM, programmed memory such as read only memory, or on a data carrier such as an optical or electrical signal carrier. Such code may be written in any conventional programming language such as C, Fourtran or assembly language. As the skilled person will appreciate such code may be distributed between a plurality of coupled components in communication with one another, for example on a network.

Thus in a further aspect the invention provides a computer program to, when running, determine a pregnant woman's risk of having a fetus with Down's syndrome, the computer comprising code to input measurement data from a measurement of at least one screening marker level from one of a first and second stage of pregnancy obtained by assaying a sample obtained from the pregnant woman at said first or second stage of pregnancy for at least one biochemical screening marker; input measurement data from a measurement of a level of the same said at least one screening marker at the other of said first and second stage of pregnancy obtained by assaying a sample obtained from the pregnant woman at said other stage of pregnancy for said at least one biochemical screening marker; and determine a quantitive estimate of the risk of Down's syndrome using the measured screening marker levels from both the first and second stages of pregnancy.

The invention also provides a computer system for providing risk data representing a likelihood of a fetus carried by a pregnant mother having a chromosomal abnormality, a first biological parameter being suitable for screening said fetus for said chromosomal abnormality, the computer system comprising: a data store operable to store data to be processed; an instruction store storing processor implementable instructions; and a processor coupled to said data store and to said instruction store and configured to load and implement said stored instructions, said instructions comprising instructions for controlling the processor to: input first data from a first stage of pregnancy of said mother, said first data comprising data representing a first value of said first biological parameter; input second data from a second, later stage of said pregnancy, said second data comprising data representing a second value of said first biological parameter; determine said risk data from said first and second data; and output said determined risk data.

These and other aspects of the invention will now be further described, by way of example only, with reference to the accompanying figures in which:

FIG. 1 shows the effects of correlation on discriminatory power of bivariate markers, in particular (a) Bivariate distribution of log(MoM PAPP-A) using parameter estimates from Wald et. al. (2003), (b) Bivariate distribution of log(MoM PAPP-A) using parameter estimates from Wald et. al. (2003) but assuming that correlations between first and second trimester values are 0.95, (c) Bivariate distribution of log (MoM PAPP-A) using parameter estimates from Wald et. al. (2003) but assuming that correlations between first and second trimester values are 0;

FIG. 2 shows effects of mean on discriminatory power of bivariate markers, in particular (a) Bivariate distribution of log(MoM PAPP-A) using parameter estimates from Wald et. al. (2003), (b) Bivariate distribution of log(MoM PAPP-A) using parameter estimates from Wald et. al. (2003) modified so that log(MoM PAPP-A) in the second trimester has the same mean as in the first trimester, (c) Bivariate distribution of log(MoM PAPP-A) using parameter estimates from Wald et. al. (2003) modified so that log(MoM PAPP-A) in the second trimester has the same mean as in the first trimester;

Figure 1A:
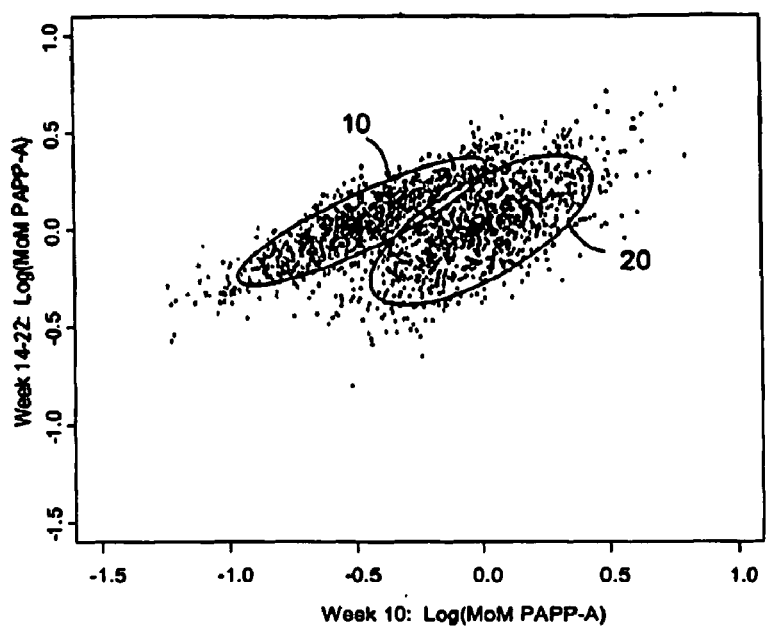
Figure 1B:
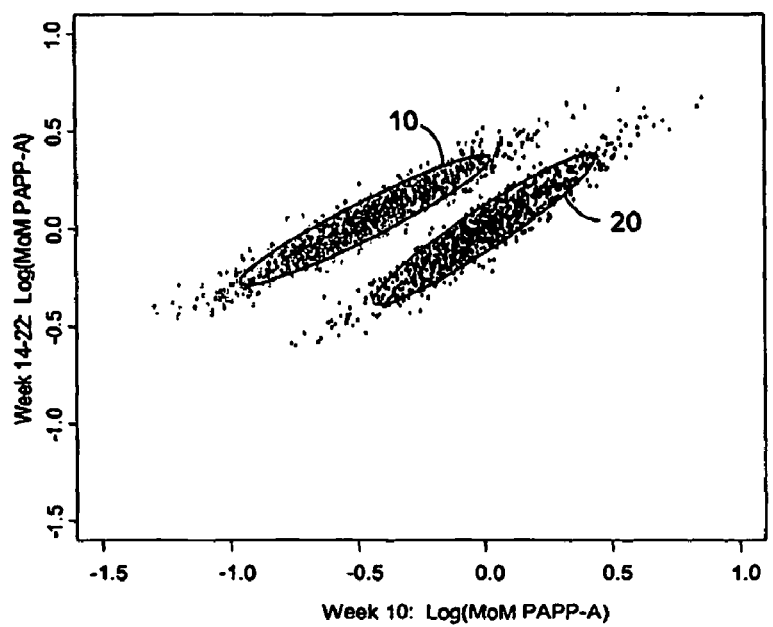
Figure 1C:
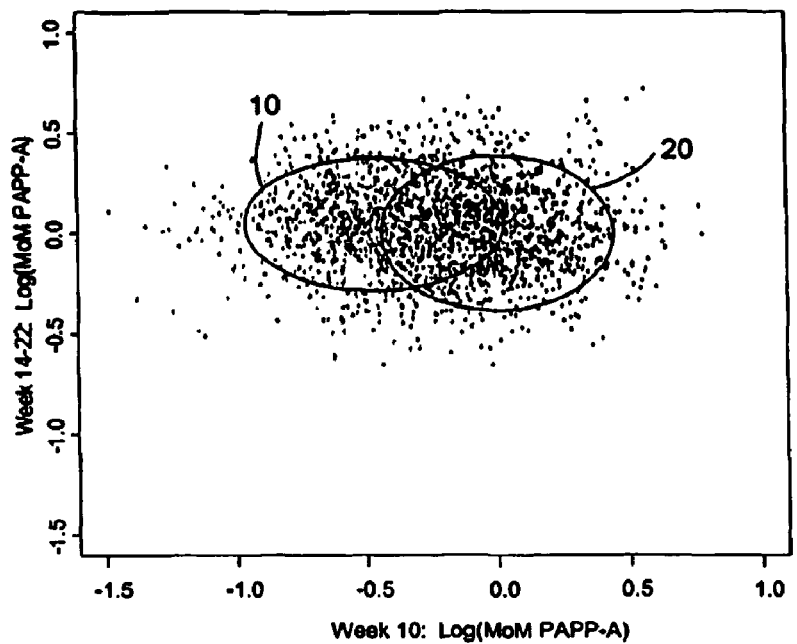
Figure 2A:
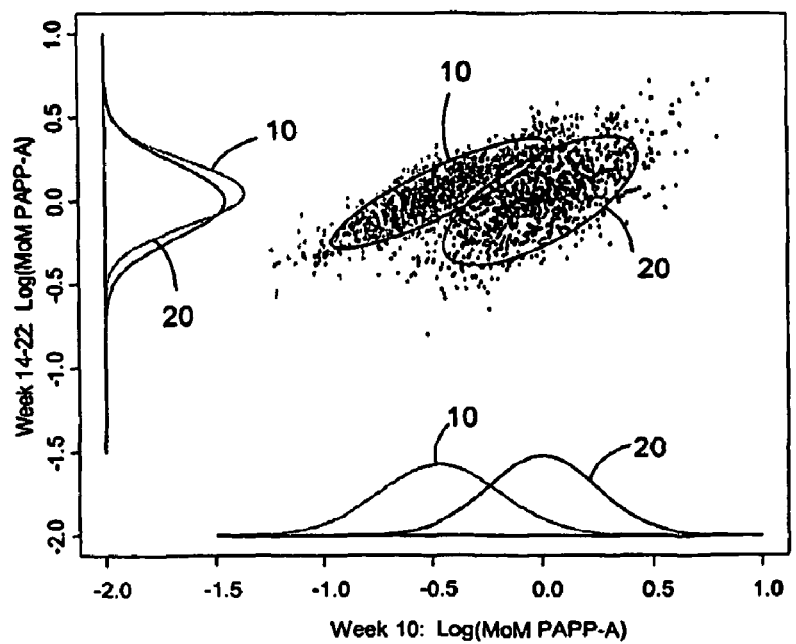
Figure 2B:
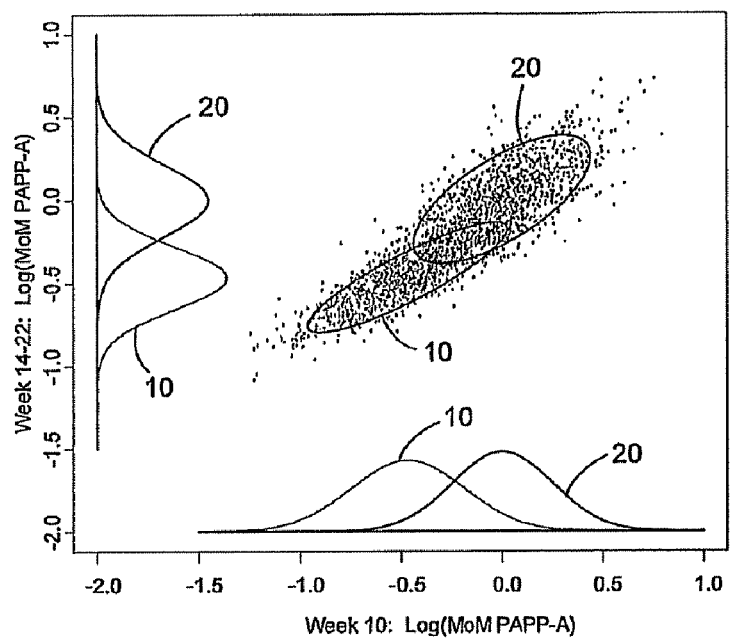
Figure 2C:
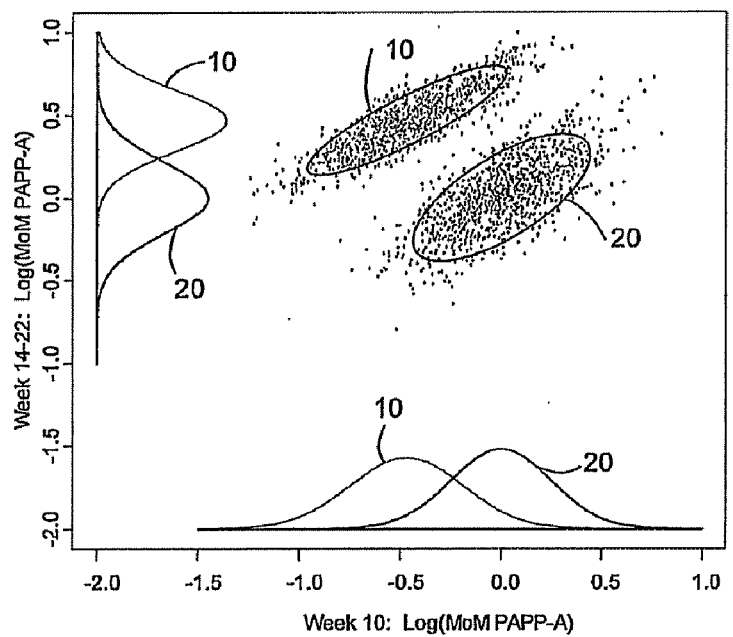
Figure 3:
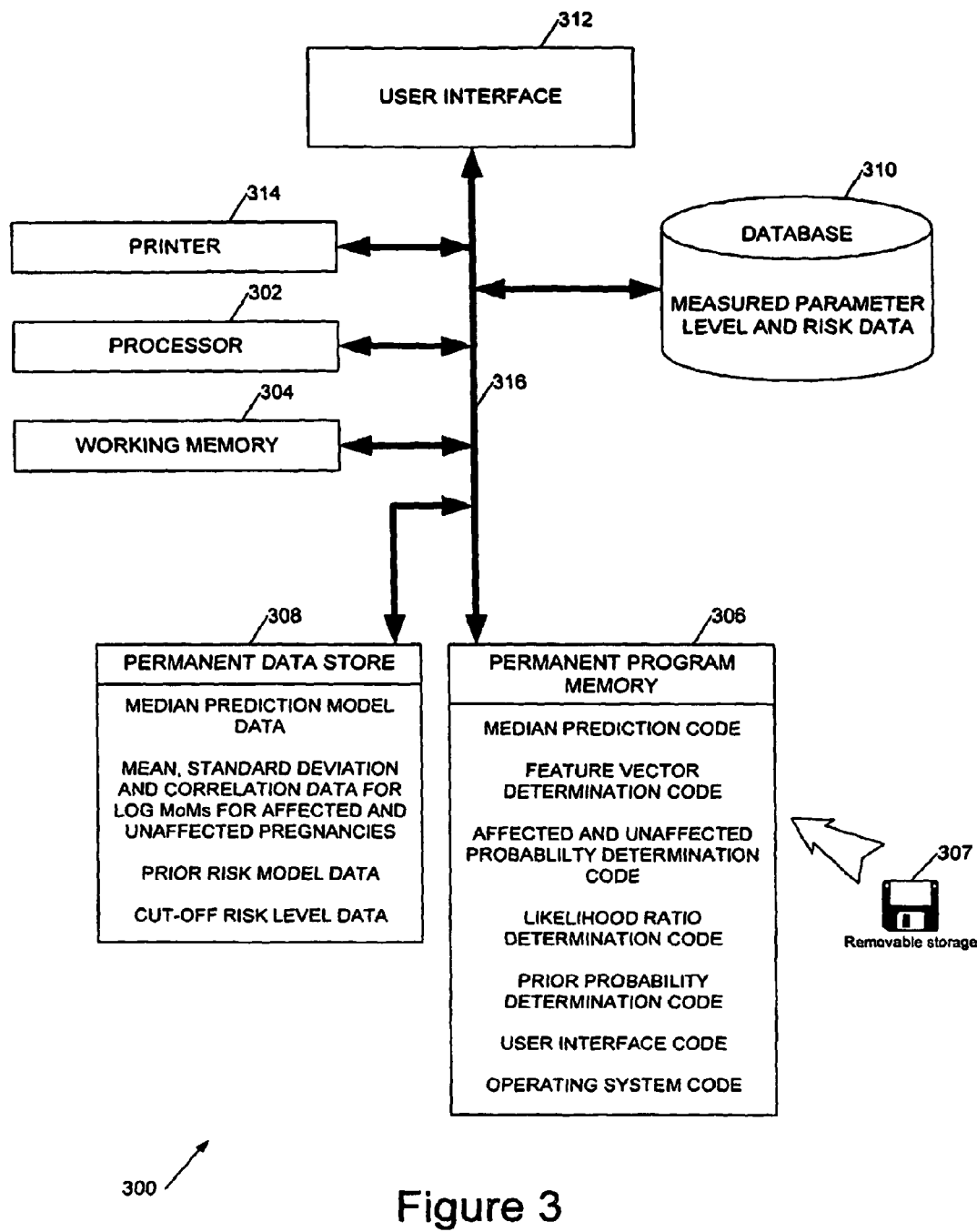
FIG. 3 shows a block diagram of a computer system for implementing a method embodying an aspect of the present invention.

Referring next to FIG. 3, this shows a block diagram of a computer system 300 configured to implement a method embodying an aspect of the present invention. A suitably programmed general purpose computer system may be employed.

The computer system comprises a processor 302 coupled to working memory 304 and to permanent programme memory 306 and permanent data memory 308 such as disk memory, Flash RAM or ROM, via a data, address and control bus 316. Autocoupled to bus 316 are user interface devices 312 such as a keyboard and pointing device and display, as well as a printer 314 and optionally (not shown) a computer network interface. Processor 302 may also be coupled to a database 310, optionally via a network, implemented on the same or a different machine.

Permanent programme memory 306 stores median prediction code, feature vector determination code, affected and unaffected probability determination code, likelihood ratio determination code, prior probability determination code, user interface code, and operating system code and processor 302 loads and implements this code to provide corresponding functions. Data memory 308 includes median prediction model data comprising regression model data for predicting median analyte values and ultrasound measurements from gestational age, maternal weight, and smoking status; mean, standard deviation, and correlation data for log MoMs (that is a vector or means, a vector of standard deviations, and matrices of correlations) for affected and unaffected pregnancies; prior risk model data; and cut-off risk level data for defining a cut-off risk level. The data in permanent programme memory 306 and/or data memory 308 may be provided on removable storage, illustratively shown by disk 307. Optional database 310 stores historical measured parameter level data for use in refining models stored in permanent data memory 308, and preferably also related calculated risk data and, optionally, data identifying whether corresponding pregnancies were in fact affected.

Figure 4:
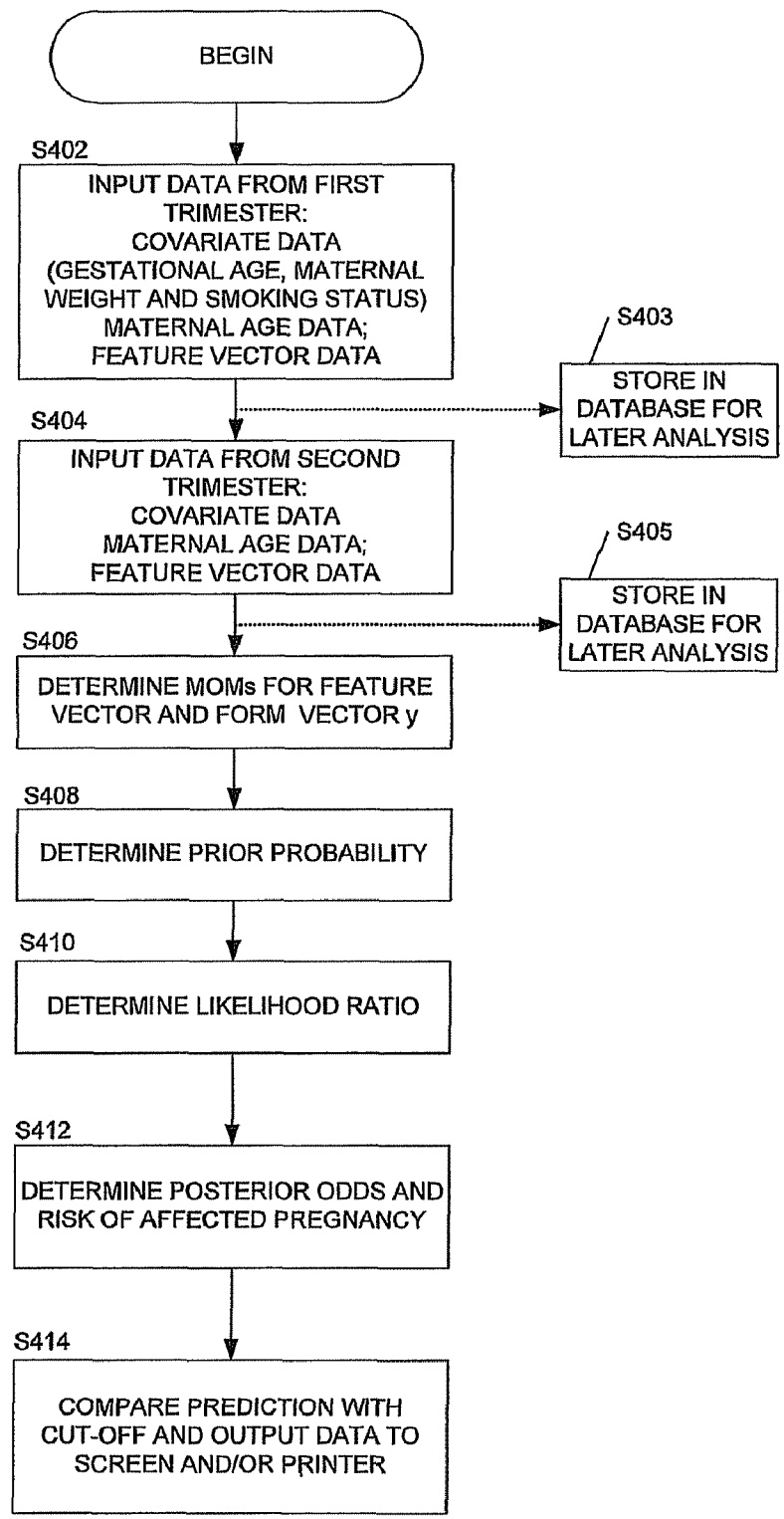
FIG. 4 shows a flow diagram for a method embodying an aspect of the present invention.

FIG. 4 shows a flow diagram illustrating a procedure for determining a risk of an affected pregnancy according to an embodiment of an aspect of the present invention; the skilled person will recognise that the steps of FIG. 4 may be performed in a different order to that illustrated in the example.

The procedure employs data gathered from both the first and second trimesters of the pregnancy. This data may either be input to the procedure in two stages or data from the first trimester may be stored until data from the second trimester is available. Data relating to levels of the various measured parameters are collected from ultrasound measurements and/or by analysing blood and/or urine samples in a conventional man$_{ner}$ according to techniques well-known in the field.

It is helpful to read the flow diagram of FIG. 4 in conjunction with table 1 below. Table 1 refers to a feature vector (that is a combination of parameters) comprising PAPP-A, total hCG, and NT but the same procedure may be employed for other combinations of parameters, for example substituting $uE_3$ for total hCG to obtain a particularly effective combination.

At step S406, for each feature vector parameter which has been input the procedure determines an MoM (Multiple of Median) and forms a feature vector y comprising a set of log MoM values from the first and second trimesters. (The MoM determination may be performed in two separate steps after inputting data from each trimester).

TABLE 1

| Trimester 1 (8 to 13 weeks) | | |
|---|---|---|
| Covariates | | |
| Gestational Age<br>Maternal weight and smoking status | ⇒ | Predicted medians for NT, Total $hCG_1$ and $PAPP-A_1$ from regression models. |
| | | ⇓ |
| Maternal Age at delivery | | |
| Feature Vector | | |
| Nuchal Translucency<br>Total $hCG_1$<br>$PAPP-A_1$ | ⇒ | MoM NT = NT/Predicted median NT<br>MOM Total $hCG_1$ = Total $hCG_1$/Predicted median Total $hCG_1$<br>MOM $PAPP-A_1$ = $PAPP-A_1$/Predicted median $PAPP-A_1$ |
| Trimester 2 (14 to 22 weeks) | | |
| Covariates | | |
| Gestational age at time of sample<br>Maternal weight and smoking status | ⇒ | Predicted medians for Total $hCG_2$ and $PAPP-A_2$ from regression models. |
| | | ⇓ |
| Feature Vector | | |
| Total $hCG_2$<br>$PAPP-A_2$ | ⇒ | MOM Total $hCG_2$ = Total $hCG_2$/Predicted median Total $hCG_2$<br>MOM $PAPP-A_2$ = $PAPP-A_2$/Predicted median $PAPP-A_2$ |
| Density for unaffected type | ⇒ | $p(y\|Unaffected)$ |
| Density for Down's syndrome type | ⇒ | $p(y\|Down's)$    $y = \begin{pmatrix} \log(MoM\ NT) \\ \log(Mom\ Total\ hCG_1) \\ \log(MoM\ Total\ hCG_2) \\ \log(MoM\ PAPPA_1) \\ \log(MoM\ PAPPA_2) \end{pmatrix}$ |
| Likelihood ratio | | $LR = \dfrac{p(y\|Unaffected)}{p(y\|Down's)}$ |
| Prior probability given maternal age m. | | $p(Down's \| m)$ |
| Prior Odds of unaffected | | $\dfrac{1 - p(Down's \| m)}{p(Down's \| m)}$ |
| Posterior Odds<br>Posterior Risk | | Prior probability given maternal age m × Likelihood ratio<br>1 in (Posterior Odds + 1) |

Referring to FIG. 4, at step S402 data is input from the first trimester comprising covariate data (gestational age of the fetus, maternal weight, maternal smoking status and optionally other maternal parameters such as maternal race); the maternal age at delivery; and feature vector data, that is values of measured parameters employed by the method in determining a risk of an affected pregnancy, in this example nuchal translucency, total hCG, and PAPP-A. Optionally this data may be stored in data space 310 for later analysis (step S403). At step S404 similar data is input for the second trimester, in particular comprising feature vector data and the gestational age of the fetus at time a biochemical sample was taken in order to determine the feature vector parameter. In this example the feature vector at the second trimester comprises the levels of total hCG and of PAPP-A. Optionally maternal weight and smoking status may again be entered, for example if there has been a change. Again this second trimester data may be stored (S405) in database 310 for later analysis.

At step S408 the procedure determines the prior probability of an affected pregnancy based upon the maternal age at delivery according to a conventional formula. At step S410 the procedure determines the probability of an unaffected pregnancy given feature vector y and the probability of an affected (Down's) pregnancy given feature vector y and then calculates the ratio of these probabilities to determine a likelihood ratio. The adjusted feature vector can be thought of as defining a point in multi-dimensional space in which two surfaces are defined, one for unaffected pregnancies, the other for affected pregnancies. At this point in space both the unaffected pregnancies surface and the affected pregnancies surface have the corresponding height representing a probability of that combination of features being associated with an unaffected and an affected pregnancy respectively. The ratio of these two heights is in effect, the likelihood ratio. The prior odds of an unaffected pregnancy are determined as shown in table 1 from the probability of an affected pregnancy at the given maternal age. For example if this probability is 0.05 the prior odds of an unaffected pregnancy are (1-0.0.5)/0.05, that is 19:1 for a 1 in 20 risk based on age. At step S412 these Posterior Odds are modified by the likelihood ratio by multiplying by the likelihood ratio so that, for example, if LR equals ⅕ (that is the probability of an unaffected pregnancy to the probability of an affected pregnancy is 1:5) then the prior odds are multiplied by ⅕ so that, for example, 1 in 20 becomes 1 in 4. At step S412 the risk of an affected pregnancy is also determined the risk being equal to 1 in (Posterior Odds+1).

Figure 5:
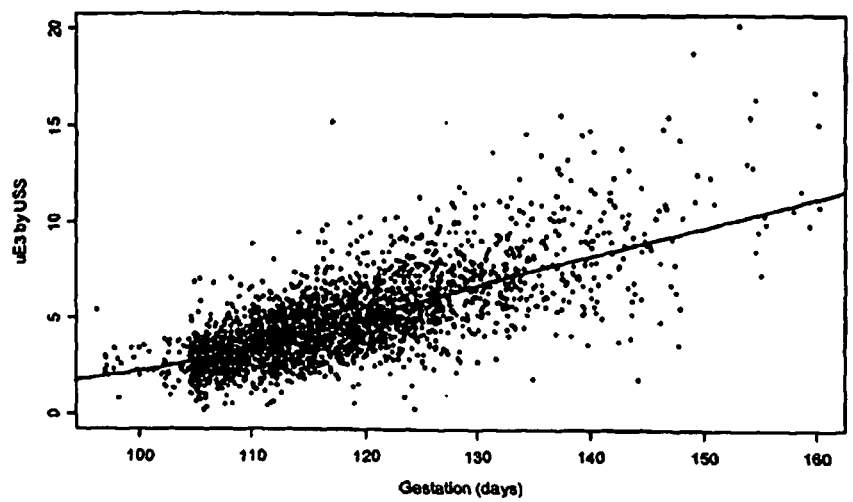
FIG. 5 shows a graph illustrating the dependency of the level of marker $uE_3$ on gestational age in days for unaffected pregnancies.

Once the posterior odds and risk have been determined at step S412 they can be compared, at step S414, with a risk cut-off and the pregnancy classified as either high (or preferably "increased") risk or low risk. The data generated by the procedure may then be output to a screen and/or printer (and/or over a computer network), for example in the form of a risk assessment report. An example of such a report is shown in table 2.

for uE3 in FIG. 5. The aim is to produce standardised values that are comparable across all gestational ages. The reference values can also take into account other covariates that influence the marker values. In particular, it has been established that levels vary with maternal weight and maternal ethnic origin and that maternal diabetes, and the presence of multiple gestations also affects the marker levels. It has also been established that some markers, particularly hCG, are influenced by smoking (Bartels, I., Hoppe-Sievert, B., Bockel, B., Herold, S. and Caesar, J (1993) "Adjustment formulae for maternal serum alpha-fetoprotein, human chorionic gonadotrophin, and unconjugated osestriol to maternal weight and smoking;" *Prenatal Diagnosis,* 13, 123-130). Division of an individual woman's results by these reference values gives each results as a multiple of the median or MoM.

For each feature variable, standardization for gestational age, and optionally maternal weight and other covariates such smoking status may be achieved through a linear or non-linear regression model. Standard linear or non-linear models may be used to obtain equations for predicting reference

TABLE 2

| First Trimester | Value | Standardized for | | | Predicted Median | Multiple of Median (MoM) |
| --- | --- | --- | --- | --- | --- | --- |
| | | Gestational age (days) | Maternal Weight (kg) | Smoking Status | | |
| NT | | | | | | |
| Total hCG | | | | | | |
| PAPP-A | | | | | | |
| Second Trimester | | | | | | |
| NT | | | | | | |
| Total hCG | | | | | | |
| PAPP-A | | | | | | |

| | |
| --- | --- |
| Maternal age at expected date of delivery: | *.* years |
| Maternal age specific risk: | 1 in **** |
| Updated risk: | 1 in **** |
| Risk cut-off: | 1 in 300 |
| Outcome: | High Risk Low Risk |

Also at step S414 a record may be written to database 310, for example in the form shown in table 3 below (where a personal ID is used in preference to, for example, a name and address for reasons of confidentiality).

TABLE 3

Personal ID
Analytes Measured
Covariates Used
Multiple of Medians
Age related Risk
Risk updated for features The steps described in the above procedure will now be described in more detail for a preferred embodiment of the risk calculation for a specific pregnancy. In what follows the measured parameters (useful as markers at one stage of pregnancy but not at another) are for convenience referred to as feature variables.

Regression Equations for Standardizing Feature Variables for Gestation and Other Covariates The first stage in the calculation of Down syndrome risk is to compare an individual woman's marker results with appropriate reference values. The main reason for this is to correct for changes marker levels with gestational age as illustrated values from data on unaffected pregnancies. Typically in these models the log transformed marker level (base 10 or base e) is regressed on gestational age maternal weight and other covariates. Detailed explanations of this regression methodology can be found in standard statistical textbooks (see, for example, Draper, N. R. and Smith, H. (1981), *Applied Regression Analysis*, Second Edition, John Wiley and Sons, New York). The methodology is also implemented in standard statistical packages such as S-PLUS.

For example, a generalised model for $uE_3$ may take the form:

$$\log(uE3_{pred}+\text{Offset})=A+B*f_1(\text{gestation})+C*f_2(\text{gestation})+D*f_3(\text{weight})+E*f_4(\text{gravidity})+F*f_5(\text{weight})*f_6(\text{gravidity})+G*f_7(\text{smoking})+H*f_8(\text{smoking})*f_9(\text{weight})$$

where:

$\log uE3_{pred}$=the (predicted) log of the reference concentration of analyte for a woman of this gestational age and with these attributes.

gestation=gestational age of the fetus in days weight=maternal weight gravidity=0 for first pregnancy, 1 for subsequent pregnancies smoking=0 for does not smoke, 1 for smokes $f_1$-$f_9$ represent functions of the variables (for example log or other power transforms).

In some implementations these transformations may involve unknown parameters that are estimated from sample data on routinely screened pregnancies.

Offset, A,B,C,D,E,F,G and H are parameters that can be estimated from reference data and/or from data stored in database 310 on pregnancies screened and later found to be unaffected. These estimates may be monitored and updated at intervals, for example as the volume of stored data grows, in order to obtain better estimates.

Local Adjustments

Effects due to maternal weight, race, gravidity and smoking are physiological responses that do not generally depend upon the specific methods (e.g. type of assay) and the population being screened. Individual screening centres may however employ a method of calibrating the regression model to reflect the methods they use and the population being screened.

The preferred approach to dealing with this is to fit the core model to extensive data and to use a simple linear regression model to calibrate the model for a specific population. This provides a degree of flexibility for the user to tailor the regression model to local populations whilst maintaining the overall structure of the model. For example, a local screening centre may fit a simple linear regression model of the form:

$$\log(uE3_{local}) = \beta_0 + \log(uE3_{pred})$$

or $$\log(uE3_{local}) = \beta_0 + \beta_1 * \log(uE3_{pred})$$

where:

$\log uE3_{local}$ is the log of the calibrated reference concentration for the local centre;

$\log(uE3_{pred})$ is the log of the reference value established from an extensive analysis of reference data; and $\beta_0$ and $\beta_1$ are estimated from local data on routine screening.

Continuous Monitoring and Updating

Where this is employed a preferred approach is to continuously monitor the log(MoM) values to identify any changes in their distribution as early as possible. If changes are detected then appropriate actions can be taken. For example, it may be desirable to update the parameters $\beta_0$ and $\beta_1$ in the above equations.

Similar models may be used for other feature variables. However it is not necessary to use a model with the complexity of the generalised model and some examples of models which may be employed (except for NT taken from Wald et al, 2003 (ibid), Table 33, NT taken from Wright, D. E. and Bray I. (2003) A Mixture Model for Rounded Data. *The Statistician*, 52, 3-13.) are as follows:

$$\text{Log(median } uE_3) = 0.414 - 5.95 \times 10^{-3}(GA)$$

$$\text{Log(median total } hCG) = -0.866 + 1.21 \times 10^{-2}(GA)$$

$$\text{Log(median free } \beta\text{-}hCG) = -0.327 + 7.68 \times 10^{-3}(GA)$$

$$\text{Log(median inhibin-}A) = -1.11 + 1.55 \times 10^{-2}(GA)$$

$$\text{Log(median } PAPP\text{-}A) = -1.14 + 9.65 \times 10^{-3}(GA)$$

$$\text{Log(median } NT) = -8.34 \times 10^{-2} + 3.93 \times 10^{-3}(CRL)$$

where GA is the gestational age of the fetus in days and CRL is the Crown-Rump Length in millimeters.

Preferably "local" data is used for establishing medians, particularly with NT for which there is an element of subjectivity.

More complex models may be employed. For example for an implementation involving repeated measures of hCG, PAPP-A and a single measure of Nuchal translucency models of the form illustrated below may be used.

Standardisation of Feature Vectors

Each measured feature or parameter is then "standardized" by representing its observed value as a multiple of the median value for that feature or marker level. This is achieved by dividing the feature variable by the median value (not the log value) predicted from the regression model described above to produce a Multiple of Median measure or MoM. The logarithm of each MoM is then taken and a feature vector y is then constructed from the set of log(MoM) values. In Down's syndrome pregnancies and in unaffected pregnancies the feature vector y is assumed to follow a multivariate normal or Gaussian distribution in p-dimensional space where p is the number of variables in the feature vector.

Likelihood Ratios

In the risk algorithm, the vector of log MoM values y in Down's syndrome pregnancies and in unaffected pregnancies is assumed to follow a multivariate normal distribution. Such a distribution is defined by a mean vector, a standard deviation vector and a correlation matrix; values of these are determined by the type of pregnancy (Down's syndrome or unaffected), by the covariates used to compute the MoM values, and by the method used to determine gestational age (LMP or ultrasound scan), as described further below.

Thus, for example, in a model comprising repeated measures of total hCG, PAPP-A and a single measure of NT the mean vector comprises means values of NT, total $hCG_1$, PAPP-$A_1$, total $hCG_2$, and PAPP-$A_2$ (where '1' and '2' denote the first and second trimesters respectively); the standard deviation vector comprises standard deviation values of NT, total $hCG_1$, PAPP-$A_1$, total $hCG_2$, and PAPP-$A_2$; and the correlation matrix has a set of rows of NT, total $hCG_1$, PAPP-$A_1$, total $hCG_2$, and PAPP-$A_2$ and a corresponding set of columns. In a model comprising repeated measures of $uE_3$, PAPP-A and a single measure of NT in the above vectors $uE_3$ is substituted for total hCG.

To determine a likelihood ratio the likelihood of y given a distribution defined by the above parameters for both affected and unaffected pregnancies is determined. Thus the mean and standard deviation vectors and the correlation matrix are defined for both affected and unaffected pregnancies in order to determine likelihood values for affected and unaffected pregnancies.

In a model comprising repeated measures of total hCG, PAPP-A and a single measure of NT the following mean and standard deviation vectors may be employed (taken from Wald et al. (2003) Appendix, Tables 33 and 34; gestational age estimated from scan; in completed weeks for mean, over 10-13 and 14-20 for standard deviations; measurements adjusted for maternal weight; means are $\log_{10}$(MoM) values).

TABLE 4a

| | | Unaffected Pregnancies | | Down's Syndrome Pregnancies | |
|---|---|---|---|---|---|
| Feature | Week | Mean Vector | Standard Deviation | Mean Vector | Standard Deviation |
| NT | 11 | 0 | 0.1439 | 0.2922 | 0.2313 |
| Total $hCG_1$ | 11 | 0 | 0.1950 | 0.1038 | 0.2069 |
| PAPP-$A_1$ | 11 | 0 | 0.2495 | −0.3768 | 0.2802 |
| Total $hCG_2$ | 14-22 | 0 | 0.2276 | 0.3118 | 0.2395 |
| PAPP-$A_2$ | 14-22 | 0 | 0.2181 | 0.0453 | 0.1872 |

In the same model the following correlation matrices may be employed (taken from Wald et al. (2003) Appendix, Tables 42 and 43; first trimester observations taken at 11 weeks gestation, second trimester observations taken between 14 and 20 weeks gestation, gestational age estimated from scan, measurements adjusted for maternal weight).

TABLE 4b

|  | NT | Total hCG$_1$ | PAPP-A$_1$ | Total hCG$_2$ | PAPP-A$_2$ |
|---|---|---|---|---|---|
| Down's |  |  |  |  |  |
| NT | 1 | −0.0819 | −0.1506 | 0.0466 | 0.0202 |
| Total hCG$_1$ |  | 1 | 0.1284 | 0.6912 | 0.1432 |
| PAPP-A$_1$ |  |  | 1 | −0.2295 | 0.8798 |
| Total hCG$_2$ |  |  |  | 1 | −0.0912 |
| PAPP-A$_2$ |  |  |  |  | 1 |
| Unaffected |  |  |  |  |  |
| NT | 1 | −0.0758 | −0.0516 | −0.0661 | −0.0625 |
| Total hCG$_1$ |  | 1 | 0.2198 | 0.7191 | 0.3853 |
| PAPP-A$_1$ |  |  | 1 | 0.0624 | 0.6895 |
| Total hCG$_2$ |  |  |  | 1 | 0.2838 |
| PAPP-A$_2$ |  |  |  |  | 1 |

In a model comprising repeated measures of uE$_3$, PAPP-A and a single measure of NT the following mean and standard deviation vectors may be employed (ibid).

TABLE 5a

|  |  | Unaffected Pregnancies | | Down's Syndrome Pregnancies | |
|---|---|---|---|---|---|
| Feature | Week | Mean Vector | Standard Deviation | Mean Vector | Standard Deviation |
| NT | 11 | 0 | 0.1439 | 0.2922 | 0.2313 |
| uE$_{3(1)}$ | 11 | 0 | 0.1204 | −0.0605 | 0.1720 |
| PAPP-A$_1$ | 11 | 0 | 0.2495 | −0.3768 | 0.2802 |
| uE$_{3(2)}$ | 14-22 | 0 | 0.1142 | −0.1549 | 0.1238 |
| PAPP-A$_2$ | 14-22 | 0 | 0.2181 | 0.0453 | 0.1872 |

In the same model the following correlation matrices may be employed (ibid; first trimester observations taken at 11 weeks gestation, second trimester observations taken between 14 and 20 weeks gestation, gestational age estimated from scan, measurements adjusted for maternal weight).

TABLE 5b

|  | NT | uE$_{3(1)}$ | PAPP-A$_1$ | uE$_{3(2)}$ | PAPP-A$_2$ |
|---|---|---|---|---|---|
| Down's |  |  |  |  |  |
| NT | 1 | 0.1240 | −0.1506 | 0.0695 | 0.0202 |
| uE$_{3(1)}$ |  | 1 | 0.3562 | 0.7356 | 0.2129 |
| PAPP-A$_1$ |  |  | 1 | 0.3712 | 0.8798 |
| uE$_{3(2)}$ |  |  |  | 1 | 0.4837 |
| PAPP-A$_2$ |  |  |  |  | 1 |
| Unaffected |  |  |  |  |  |
| NT | 1 | 0.0662 | −0.0516 | 0.0596 | −0.0625 |
| uE$_{3(1)}$ |  | 1 | 0.1009 | 0.5803 | 0.0815 |
| PAPP-A$_1$ |  |  | 1 | 0.1213 | 0.6895 |
| uE$_{3(2)}$ |  |  |  | 1 | 0.0983 |
| PAPP-A$_2$ |  |  |  |  | 1 |

Further values for mean and standard deviation vectors and for correlation matrices may be taken from the Appendix of Wald et al. Health Technology Assessment 2003, volume 7(11), (UK National Health Service R&D HTA Programme) available from www.ncchta.org and from The National HTA Coordinating Centre, Mailpoint 728, Boldrewood, University of Southampton SO16 7PX, UK. In particular:

Table 33: Mean(log$_{10}$(MoM)) values for Down's pregnancies, according to gestational age;

Table 34: Standard deviation values for first and second trimesters, for Down's and unaffected pregnancies, adjusted for maternal weight (except NT which does not vary with maternal weight), for gestational age estimate based on LMP and on (ultrasound) scan;

Table 35: Standard deviation values for urine markers for first and second trimesters, for Down's and unaffected pregnancies, adjusted for maternal weight, for gestational age based on scan;

Table 36: Correlation coefficients for Down's pregnancies for gestational age estimate based on LMP, not adjusted for maternal weight;

Table 37: Correlation coefficients for unaffected pregnancies for gestational age estimate based on LMP, not adjusted for maternal weight;

Table 38: Correlation coefficients for Down's pregnancies for gestational age estimate based on LMP, adjusted for maternal weight;

Table 39: Correlation coefficients for unaffected pregnancies for gestational age estimate based on LMP, adjusted for maternal weight;

Table 40: Correlation coefficients for Down's pregnancies including NT, for gestational age estimate based on scan, not adjusted for maternal weight;

Table 41: Correlation coefficients for unaffected pregnancies including NT, for gestational age estimate based on scan, not adjusted for maternal weight;

Table 42: Correlation coefficients for Down's pregnancies including NT, for gestational age estimate based on scan, adjusted for maternal weight; and Table 43: Correlation coefficients for unaffected pregnancies including NT, for gestational age estimate based on scan, adjusted for maternal weight;

the data from these tables being specifically incorporated herein by reference.

In the general case the value of, say, a mean may be expressed as a model in a similar way to a feature variable:

$$\mu = \alpha_0 + \alpha_1(\text{GestationalAge}) + \alpha_2(\text{GestationalAge})^2 + \alpha_3(\text{MaternalWeight}) + \ldots$$

In a similar way to that described for feature variables data stored in database 310 may be used to determine improved estimates for the a$_1$ values in such an expression as the volume of stored data grows.

Multivariate Normal Probability Density Function

The above mentioned multivariate normal distribution for a p dimensional vector of log(MoM) values y is defined in terms of a mean vector μ and a covariance matrix Σ (in terms of log(MoM) values) and is given by:

$$p(y|\mu, \Sigma) = (2\pi)^{-\frac{p}{2}}|\Sigma|^{-\frac{1}{2}}\exp(-(y-\mu)^T\Sigma^{-1}(y-\mu)) \quad \text{Equation 1}$$

where μ is a p vector of means, p(y|μ,Σ) denotes the probability of y given μ,Σ, and superscripts 'T' and '−1' denote transpose and matrix inversion respectively. As can be understood from the above data, μ is dependent on type of pregnancy and on stage of pregnancy (i.e. first or second trimester). For unaffected pregnancies, μ=0 (where 0 denotes a p-vector of zeros) at both stages.

Σ is a symmetric p×p covariance matrix which, as can be understood from the above data and examples, is dependent on type of pregnancy, stage, the method of obtaining gestational age and on which covariates (e.g. maternal weight and smoking status) are used in the calculation of medians. In general, the inclusion of additional covariates reduces dispersion.

The covariance matrix Σ is generally specified in terms of a vector of standard deviations s and a correlation matrix R. It is calculated as the matrix product below in which diag(s) denotes the p×p matrix with diagonal elements corresponding to the elements of the standard deviation vector and zeros elsewhere, as shown in Equation 2 below.

$$\Sigma = diag(s) R\ diag(s) \quad \text{Equation 2}$$

Values of μ, s and R, estimated from samples of data on unaffected and Down's syndrome pregnancies, can be obtained from a number of sources including Wald et al. (2003) as detailed above. In the case of PAPP-A the value of μ in Down's syndrome pregnancies during the first trimester depends on gestational age as shown in Table 6 below (data from Wald et al., Table 33) and therefore a value for μ appropriate for the gestational age at which PAPP-A was measured should preferably be employed.

TABLE 6

| | Completed week of pregnancy | | | |
|---|---|---|---|---|
| $Log_{10}(MoM)$ | 10 | 11 | 12 | 13 |
| PAPP-A | −0.4685 | −0.3768 | −0.3010 | −0.2366 |

Using Equation 1 values are determined for p(y|Unaffected) and p(y|Down's) and then a likelihood value ratio is calculated according to Equation 3:

$$LR = \frac{p(y\ |\ \text{Unaffected})}{p(y\ |\ \text{Down's})} \quad \text{Equation 3}$$

Age Specific (Prior) Odds Ratios

Maternal age specific risks of Down's syndrome may be obtained from an established model such as Wright, D. E. and Bray, I. (2000) "Estimating birth prevalence of Down syndrome", *Journal of Epidemiology and Biostatistics*, 5, 89-97. In this model the live birth prevalence of Down's syndrome for a pregnancy with expected maternal age at date of delivery m is given by $$p(\text{Down's}\ |\ m) = \\ 0.000681 + \frac{(1 - 0.000681)}{1 + \exp(16.26373 - 0.2901614(m - 0.5))} \quad \text{Equation 4}$$

Optionally other risk factors such as smoking, diabetes and the like may also be incorporated into the prior risk model as mentioned above.

The odds ratio (unaffected/affected) is then given by:

$$\frac{1 - p(\text{Down's}\ |\ m)}{p(\text{Down's}\ |\ m)} \quad \text{Equation 5}$$

Posterior Odds Ratio

The posterior odds of an unaffected pregnancy may be obtained from the age specific prior odds and the likelihood ratio:

Posterior Odds=Prior Odds×Likelihood Ratio   Equation 6

The posterior risk of Down's syndrome may then be obtained from the posterior odds using Equation 7 below:

Posterior Risk=1 in(1+Posterior Odds)   Equation 7

Following this a Risk Assessment Report may be provided, for example as shown in Table 2 above.

A non-comprehensive list of markers which may be employed in embodiments of the method is given below:

TABLE 7

| In Maternal Serum or Plasma: |
|---|
| Alpha feto-protein (AFP) |
| Unconjugated osetriol ($uE_3$) |
| Human chrionic gonadotrophin (hCG) |
| Free alpha sub-unit of hCG (free α-hCG) |
| Free beta sub-unit of hCG (free β-hCG) |
| Inhibin, preferably dimeric inhibin-A (inhibin A) |
| Pregnancy-associated plasma protein A (PAPP-A) |
| In maternal Urine: |
| Beta-core hCG |
| Total oestriol |
| Ultrasound Markers: |
| Nuchal translucency (NT) thickness, nuchal fold thickness |
| Femul length |
| Humerus length |
| Hyperechogenic bowel |
| Renal pyelectasis |
| Fetal heart rate |
| Certain cardiac abnormalities |

However as well as the features (markers) mentioned above (and combinations thereof) other potentially useful biological parameters may have previously been dismissed because of relatively high correlation with other known, preferred markers. These form a pool of potential further markers that may also be employed in embodiments of the method either alone or in combination with one or more of the above mentioned markers.

Obtaining samples from and/or making measurements on the mother are generally performed by qualified medical personnel in accordance with conventional medical practice. Maternal serum, plasma, and urine samples may be refrigerated for assaying for a biochemical marker sometime after their collection.

Referring to the maternal serum/plasma markers in the above table, all except PAPP-A are effective as markers during the second trimester of pregnancy (14-22 weeks) but not during the first trimester (8-13 weeks), whereas PAPP-A is effective during the first trimester but not during the second. Nuchal translucency measurements are effective during the first trimester but not the second.

The effectiveness of some biochemical markers may be determined from the MoM data in Table 33 of Wald et al (Health Technology Assessment 2003; vol 7 no 11), hereby incorporated by reference. The effectiveness of a biochemical marker generally varies relatively smoothly over time (although the effectiveness of PAPP-A falls dramatically at the end of the first trimester of pregnancy). Thus a marker may be considered ineffective in the first stage or trimester of pregnancy if, for a human, the effectiveness of the marker at week 10 of the first trimester is different by a factor of at least five to the effectiveness of the marker during the second trimester of pregnancy (measured in terms of a median marker level ($log_{10}$ MoM)). A significant difference in the effectiveness of a marker (perhaps better called a feature in this context) between two different stages of pregnancy enables improved test performance lower false positive rate).

Table 8, below (based on Wald et al. (2003) Tables 33, 34, 42), illustrates that a number of features have potentially useful characteristics in that a) first and second trimester log (MoM) values are highly correlated in both Down's syndrome and unaffected pregnancies and (b) they discriminate in one trimester but not the other. In Table 8 MoM values are obtained from scan based estimates of gestational age and are corrected for weight; trimester 1 data is taken at 10 completed weeks and trimester 2 data for weeks 14-22). Bold values indicate useful discrimination. For the sake of completeness data for NT has also been included. Particularly useful features include PAPP-A, total hCG, $uE_3$, and inhibin-A.

Figure 7:
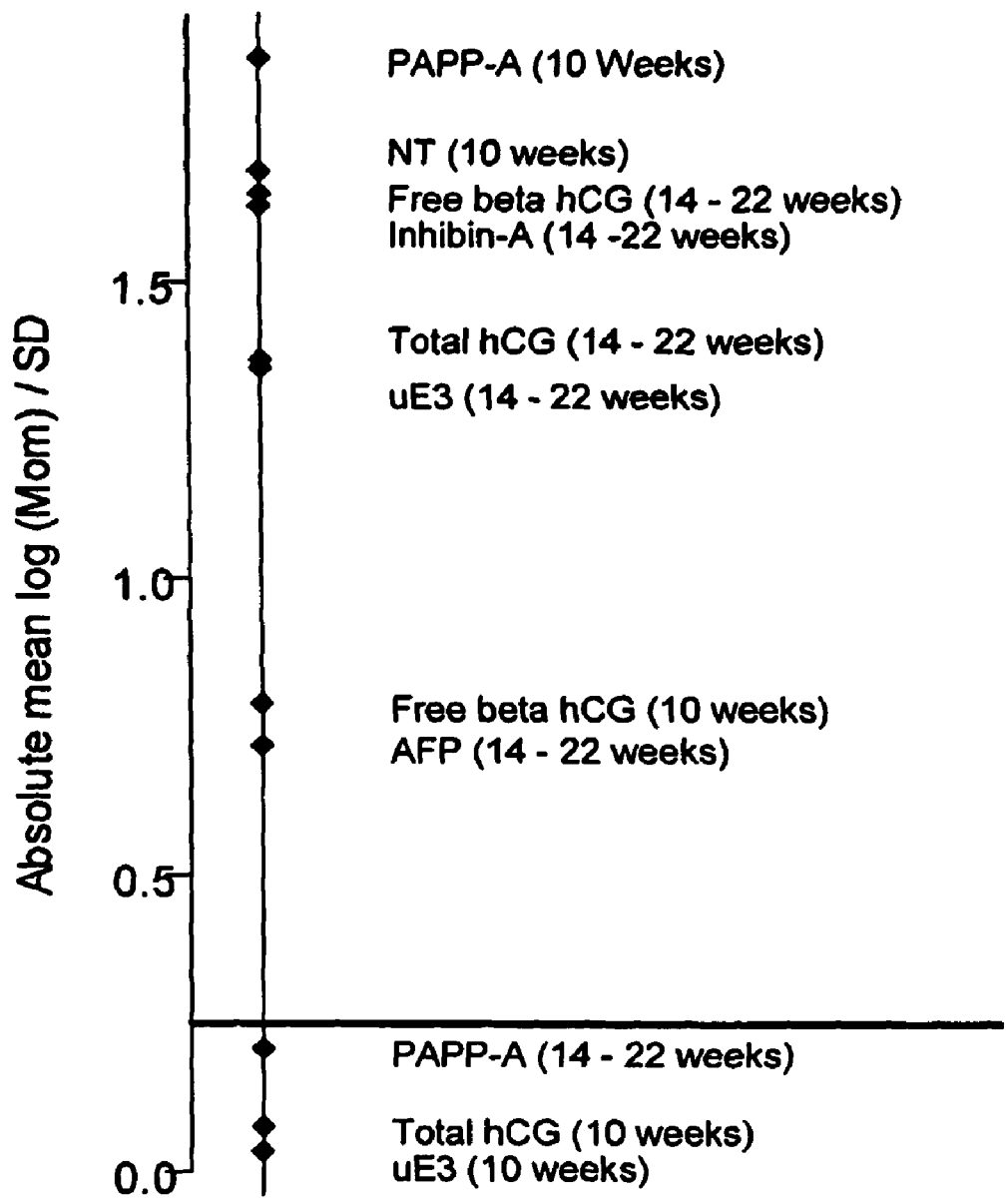
FIG. 7 shows a graphical depiction of absolute mean log (MoM) values as a proportion of standard deviation (SD).

FIG. 7 shows a graphical depiction of absolute mean log (MoM) values in Table 8 as a proportion of standard deviation (SD); the solid horizontal line indicates 0.25SD, which may be taken as a threshold below which a feature is substantially ineffective as a marker. It can be seen that for these features there is a clear distinction between those effective as markers at a given stage and those that are substantially ineffective.

TABLE 8

|  | Trimester 1 | | Trimester 2 | | |
| --- | --- | --- | --- | --- | --- |
|  | Mean (log (MoM)) | Standard Deviation | Mean (log (MoM)) | Standard Deviation | Correlation |
| Down's syndrome | | | | | |
| PAPP-A | −0.4685 | 0.2802 | 0.0453 | 0.1872 | 0.8798 |
| Inhibin A | −0.0269 | 0.2343 | 0.3384 | 0.2679 | 0.6269 |
| Total hCG | −0.0177 | 0.2069 | 0.3118 | 0.2395 | 0.6912 |
| AFP | −0.0655 | 0.1672 | −0.1308 | 0.1398 | 0.5003 |
| uE3 | −0.0044 | 0.1720 | −0.1549 | 0.1238 | 0.7356 |
| NT | 0.2922 | 0.2313 | | | |
| Unaffected | | | | | |
| PAPP-A | 0 | 0.2495 | 0 | 0.2181 | 0.6895 |
| Inhibin A | 0 | 0.2191 | 0 | 0.2078 | 0.7003 |
| Total hCG | 0 | 0.1950 | 0 | 0.2276 | 0.7191 |
| AFP | 0 | 0.1818 | 0 | 0.1399 | 0.5587 |
| uE3 | 0 | 0.1204 | 0 | 0.1142 | 0.5803 |
| NT | 0 | 0.1732 | | | |

One way of determining the detection rate and false positive rate for a test with a specific risk cut-off is as follows. For each of a set of ages it is straightforward to determine the value of likelihood ratio beyond which a pregnancy will screen positive. A large number, say 100,000, of random draws is made from the multivariate Gaussian distribution of the log MoM values y in unaffected pregnancies. The proportion of these draws giving positive results for a particular maternal age is the false positive proportion. This proportion is calculated for a sequence of maternal ages 12, 13, . . . 50, to produce a false positive proportion for each maternal age. A weighted average of these proportions is formed with the weights proportional to the unaffected maternal age distribution of the population of interest. For example, if one in fifty of unaffected women have a maternal age of 25 then the false positive rate for women of 25 is weighted by a factor of 1/50 to provide an average weighted for a population profile. A similar approach is used to determine the detection rate. In this case draws are made from the multivariate Gaussian distribution of the log MoM values y in Down's syndrome pregnancies and the weights are proportional to the Down's syndrome maternal age distribution. By altering the cut-off value used, the ROC performance of the screening procedure can be obtained and the false positive rate for a fixed detection rate or conversely the detection rate for a fixed false positive rate can be established. This approach has advantages over alternative techniques such as numerical integration in that errors due to the sampling can be quantified statistically and the number of draws can be determined to achieve the desired precision.

The screening performance of various combinations of features were assessed taking the distribution of maternal ages for the three years from 1996 to 1998 (live births in England and Wales) and integrating the multivariate Gaussian density to provide estimates of detection rates and false positive rates for various risk cut-off's. This is the same methodology as Wald et al. (2003). The results for selected combinations of features are given in Table 9.

TABLE 9

|  | Markers includes | False positive rate |
| --- | --- | --- |
| Repeated measures | AFP^2 | 42% |
|  | UE3^2 | 17% |
|  | Total hCG^2 | 12.9% |
|  | PAPP-A^2 | 1.9% |
|  | Inhibin-A^2 | 12.0% |
|  | Total hCG^2 + PAPP-A^2 | 1.0% |
|  | Total hCG^2 + Inhibin-A^2 | 5.5% |
|  | Total hCG^2 + uE3 | 5.5% |
|  | PAPP-A^2 + Inhibin-A^2 | 0.8% |
|  | PAPP-A^2 + uE3^2 | 0.5% |
|  | Total hCG^2 + PAPP-A^2 + Inhibin-A^2 (6) | 0.6% |
|  | Total hCG^2 + PAPP-A^2 + uE3^2 (6) | 0.1% |
|  | PAPP-A^2 + Inhibin-A^2 + uE3^2 (6) | 0.1% |
| Repeated measures + NT | Free β-hCG^2 + PAPP-A^2 + NT | 0.7% |
|  | Total hCG^2 + Inhibin-A^2 + NT (NT + 4) | 0.4% |
|  | Total hCG^2 + PAPP-A^2 + NT (NT + 4) | 0.4% |
|  | PAPP-A^2 + Inhibin-A^2 + NT (NT + 4) | 0.5% |
|  | PAPP-A^2 + uE3^2 + NT (NT + 4) | 0.1% |

In Table 9 the notation ^2 is used to represent repeated measures of a particular feature so, for example, PAPP-A^2 denotes first and second trimester PAPP-A. All characteristics presented in Table 9 assume that MoMs are based on scan gestational ages with weight adjustments, and first trimester samples are taken at 10 weeks gestation; the numbers in brackets give the number of biochemical features employed. Like the results presented by Wald et al (2003), the performance characteristics presented in Table 9 are based on the assumption that the multivariate Gaussian distribution holds and in a limited size sample andon a limited size sample.

The results may be compared with the integrated test of Wald et al. (2003) (NT and PAPP-A at 10 completed weeks; AFP, $uE_3$, free β-hCG and inhibin-A at 14-20 weeks) that has a false positive rate of 1.2% for a detection rate of 85%. The performance of many of the repeated measures tests is far superior to the integrated test (the relatively poor performance of Free β-hCG^2+PAPP-A^2+NT arises because free β-hCG is a relatively useful marker during both the first and second trimesters). In particular, the following repeated measures tests with just four features have better screening performance than the integrated test that incorporates six features including NT:

Total $hCG$^2+PAPP-$A$^2

Total $hCG$^2+Inhibin-$A$^2

PAPP-$A$^2+$uE3$^2

When NT is added or six features are included performance of the repeated measures test are improved further.

A 1.2% false positive rate means that amongst 600,000 unaffected pregnancies screened, some 1.2%×600,000=7,200 would falsely screen positive. These pregnancies would be investigated using amniocentesis at a cost of about £530 per pregnancy; the total cost of amniocentesis would be £3.8 m. Further, an expected 72 (i.e. 1%) of the unaffected pregnancies would miscarry as a result of the amniocentesis. However the repeated measures test using first and second trimester measures of $uE_3$ and PAPP-A, together with a single measure of the ultrasound marker NT, has a false positive rate of 0.1%. Amongst 600,000 unaffected pregnancies there would be some 600 false positives reducing the costs of amniocentesis from £3.8 m to approximately £0.3 m and the number of unaffected pregnancies lost through procedurally related miscarriages from 72 to 6.

Figure 6:
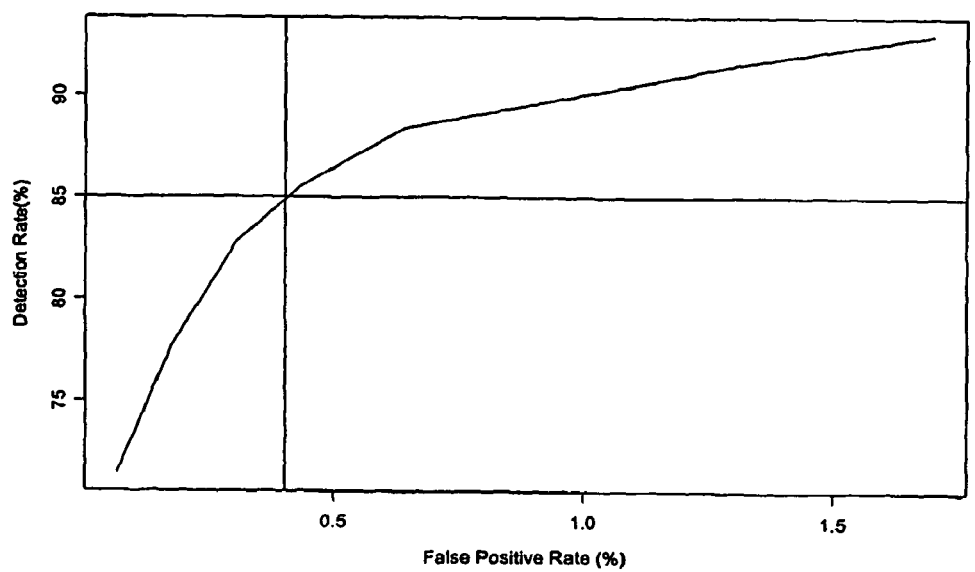
FIG. 6 shows an ROC curve for a screening process employing data from a nuchal translucency measure together with repeated measures of PAPP-A and total hCG, showing variation in detection rate (%) with false positive rate (%)

FIG. 6 shows an example of an ROC curve, showing the relationship between detection rate and false positive rate for the example of total hCG^2+PAPP-A^2+NT. Similar curves may be determined for other combinations of markers. The graph illustrates that, in this example, a false positive rate of 0.4% corresponds to a detection rate of 85%. It will be appreciated that for a given permitted false positive rate, for example 1.2%, the detection rate may be increased, in this example to over 90%, and more when using a repeated measure of $uE_3$.

No doubt many other effective alternatives will occur to the skilled person. For example, the screening procedure may be modified so that, in the first trimester, those pregnancies that are identified as being Down's syndrome with a high degree of certainty are screened positive at that stage. The remaining pregnancies then go on to the repeated measure screen. This helps to avoid an unnecessary wait until the second trimester, which is beneficial for the parents.

It will be understood that the invention is not limited to the described embodiments and encompasses modifications apparent to those skilled in the art lying within the spirit and scope of the claims appended hereto.

The invention claimed is:

1. A method of determining a likelihood of a fetus carried by a pregnant mother having a chromosomal abnormality using a first biological parameter and a second biological parameter, both of which parameters are suitable for screening said fetus for said chromosomal abnormality, the method comprising:
receiving first data from a first stage of pregnancy of said mother, said first data comprising data representing a first value of said first biological parameter which is PAPP-A, and data representing a first value of said second biological parameter, said second biological parameter comprising one of total hCG, Inhibin-A, AFP, and $uE_3$;
receiving second data from a second, later stage of said pregnancy, said second data comprising data representing a second value of said first biological parameter and data representing a second value of said second biological parameter;
wherein said first biological parameter is a marker for said chromosomal abnormality at the first stage of pregnancy and has substantially no value as a marker during the second stage of pregnancy, and
wherein said second biological parameter is a marker for said chromosomal abnormality at said second stage of pregnancy and has substantially no value as a marker during the first stage of pregnancy,
determining, using a computer, a multiple of median value for each of said values in said first and second data by dividing each of said values in said first and second data by a corresponding predicted median value;
forming, using a computer, a feature vector y using said multiple of median values;
determining a probability of an unaffected pregnancy given feature vector y;
determining a probability of an affected pregnancy given feature vector y, and
determining likelihood ratio data from said first and second data by calculating, using a computer, a ratio of said probability of an unaffected pregnancy to said probability of an affected pregnancy, said likelihood ratio data representing the likelihood of said fetus having a chromosomal abnormality.

2. A method as claimed in claim 1 wherein said first biological parameter has a logarithm multiple of median (log MoM) value closer than one standard deviation to zero.

3. A method as claimed in claim 1, wherein in a cohort of pregnancies having said abnormality said first biological parameter is selected such that a correlation coefficient of said first and second values of said parameter is greater than 0.3.

4. A method as claimed in claim 1 wherein in a cohort of pregnancies having said abnormality said second biological parameter is selected such that a correlation coefficient of said first and second values of said parameter is greater than 0.3.

5. A method as claimed in claim 1 wherein said first data further comprises data obtained from an ultrasound scan performed on said mother.

6. A method as claimed in claim 1 further comprising adjusting said first and second data responsible to one or more covariates prior to determining said likelihood ratio.

7. A method as claimed in claim 1 further comprising adjusting said likelihood ratio by a prior probability factor dependent upon an age of said mother.

8. A method as claimed in claim 1 wherein said first stage of pregnancy comprises a first trimester of said pregnancy and said second stage of said pregnancy comprises a second trimester of said pregnancy.

9. A method as claimed in claim 1 wherein said first stage of pregnancy comprises a stage of said pregnancy from 8 to 13 weeks, and wherein said second stage of said pregnancy comprises a stage of said pregnancy from 14 to 22 weeks.

10. A method as claimed in claim 1 wherein said fetus is a human fetus.

11. A method as claimed in claim 1 wherein said chromosomal abnormality comprises Down's Syndrome.

12. A method of determining whether a pregnant woman is at an increased risk of having a fetus with Down's Syndrome, the method comprising the steps of:
measuring a first screening marker level from a first stage of pregnancy by assaying a sample obtained from the pregnant woman at said first stage of pregnancy for a first biochemical screening marker, which first screening marker is PAPP-A;
measuring a level of the same said first screening marker at a second stage of pregnancy by assaying a sample obtained from the pregnant woman at said second stage of pregnancy for said at least one biochemical screening marker;
measuring a second screening marker level from said first stage of pregnancy by assaying a sample obtained from the pregnant woman at said first stage of pregnancy for said second biochemical screening marker, said second screening marker comprising one of total hCG, Inhibin-A, AFP, and $uE_3$;
measuring a level of said second screening marker at said second stage of pregnancy by assaying a sample obtained from the pregnant woman at said second stage of pregnancy for said second biochemical screening marker;

wherein said first biochemical screening marker is a marker for said chromosomal abnormality at the first stage of pregnancy and has substantially no value as a marker during the second stage of pregnancy, and wherein said second biochemical screening marker is a marker for said chromosomal abnormality at said second stage of pregnancy and has substantially no value as a marker during the first stage of pregnancy, determining, using a computer, a quantitative estimate of the risk of Down's Syndrome using the measured screening marker levels from both the first and second stages of pregnancy by expressing each of said measured screening marker levels as a logarithm of a multiple median value by dividing each of said measured screening marker levels by a corresponding predicted median value to form a feature vector y; and determining said quantitative estimate from a ratio of a probability of an unaffected pregnancy given feature vector y and a probability of an affected pregnancy in which said fetus has said abnormality given feature vector y.

13. A method as claimed in claim 12 wherein said measured screening marker levels from said first and second stages of pregnancy are highly correlated with one another.

14. A method as claimed in claim 12 wherein said measured second screening marker levels from said first and second stages of pregnancy are highly correlated with one another.

15. A method as claimed in claim 12 further comprising:
measuring at least one ultrasound screening marker from an ultrasound scan taken at one of said first and second stages of pregnancy; and
wherein determining determines said Down's risk estimate further using said ultrasound screening marker.

16. A computer system for providing risk data representing a likelihood of a fetus carried by a pregnant mother having a chromosomal abnormality using a first biological parameter and a second biological parameter, both of which parameters are suitable for screening said fetus for said chromosomal abnormality, the computer system comprising:
a data store operable to store data to be processed;
an instruction store storing processor implementable instructions; and
a processor coupled to said data store and to said instruction store and configured to load and implement said stored instructions, said instructions comprising instructions for controlling the processor to:
input first data from a first stage of pregnancy of said mother, said first data comprising data representing a first value of said first biological parameter which is PAPP-A, and data representing a first value of a second biological parameter, said second biological parameter comprising one of total hCG, Inhibin-A, AFP, and $uE_3$;
input second data from a second, later stage of said pregnancy, said second data comprising data representing a second value of said first biological parameter and data representing a second value of a second biological parameter;
determine said risk data from said fast and second data by expressing each of said first and second data as a logarithm of a multiple median value by dividing each of said first and second data by a corresponding predicted median value to form a feature vector y;

determine said likelihood ratio data from a ratio of a probability of an unaffected pregnancy given feature vector y and a probability of an affected pregnancy in which said fetus has said abnormality given feature vector y; and
output said determined risk data,
wherein said first biological parameter is a marker for said chromosomal abnormality at the first stage of pregnancy and has substantially no value as a marker during the second stage of pregnancy, and
wherein said second biological parameter is a marker for said chromosomal abnormality at said second stage of pregnancy and has substantially no value as a marker during the first stage of pregnancy.

17. A method as claimed in claim 1, wherein in a cohort of pregnancies having said abnormality said first biological parameter is selected such that a correlation coefficient of said first and second values of said parameter is greater than 0.6.

18. A method as claimed in claim 1, wherein in a cohort of pregnancies having said abnormality said second biological parameter is selected such that a correlation coefficient of said first and second values of said parameter is greater than 0.6.

19. The method of claim 1 comprising a third biological parameter,
said first data comprising data representing a first value of said third biological parameter, said third biological parameter comprising one of total hCG, Inhibin-A, AFP, and $uE_3$, said third biological parameter being different than said second biological parameter; and
said second data comprising data representing a second value of said third biological parameter,
wherein said third biological parameter is a marker for said chromosomal abnormality at said second stage of pregnancy and has substantially no value as a marker during the first stage of pregnancy.

20. The method of claim 12, comprising:
measuring a third biochemical screening marker level from said first stage of pregnancy by assaying a sample obtained from the pregnant woman at said first stage of pregnancy for said third biochemical screening marker, said third biochemical screening marker comprising one of total hCG, Inhibin-A, AFP, and $uE_3$, said third biochemical screening marker being different than said second biochemical screening marker; and
measuring a level of said third biochemical screening marker at said second stage of pregnancy by assaying a sample obtained from the pregnant woman at said second stage of pregnancy for said third biochemical screening marker;
wherein said third biochemical screening marker is a marker for said chromosomal abnormality at said second stage of pregnancy and has substantially no value as a marker during the first stage of pregnancy.

21. The computer system of claim 16 comprising a third biological parameter,
said first data representing a first value of said third biological parameter, said third biological parameter comprising one of total hCG, Inhibin-A, AFP, and $uE_3$, said third biological parameter being different than said second biological parameter; and
said second data comprising data representing a second value of said third biological parameter,
wherein said third biological parameter is a marker for said chromosomal abnormality at said second stage of pregnancy and has substantially no value as a marker during the first stage of pregnancy.

* * * * *